United States Patent
Valsesia et al.

(10) Patent No.: US 11,933,740 B2
(45) Date of Patent: Mar. 19, 2024

(54) METHOD FOR THE DETECTION AND QUANTIFICATION OF NANO OR MICRO PLASTIC PARTICLES

(71) Applicant: The European Union, represented by the European Commission, Brussels (BE)

(72) Inventors: Andrea Valsesia, Ranco (IT); Grigore Rischitor, Brussels (BE); Douglas Gilliland, Comabbio (IT); Jessica Ponti, Travedona Monate (IT); Francesco Fumagalli, Cassago in Brianza (IT); Monica Quarato, Noci (IT); Pascal Colpo, Angera (IT); Isaac Ojea Jimenez, Munich (DE)

(73) Assignee: THE EUROPEAN UNION, REPRESENTED BY THE EUROPEAN COMMISSION, Brussels (BE)

( * ) Notice: Subject to any disclaimer, the term of this patent is extended or adjusted under 35 U.S.C. 154(b) by 329 days.

(21) Appl. No.: 17/427,421

(22) PCT Filed: Jan. 30, 2020

(86) PCT No.: PCT/EP2020/052309
§ 371 (c)(1),
(2) Date: Jul. 30, 2021

(87) PCT Pub. No.: WO2020/157208
PCT Pub. Date: Aug. 6, 2020

(65) Prior Publication Data
US 2022/0136980 A1    May 5, 2022

(30) Foreign Application Priority Data
Jan. 30, 2019 (EP) .................................... 19154521

(51) Int. Cl.
*G01N 21/94* (2006.01)
*G01N 1/28* (2006.01)
(Continued)

(52) U.S. Cl.
CPC ............ *G01N 21/94* (2013.01); *G01N 1/2813* (2013.01); *G01N 21/65* (2013.01); *G01N 23/2251* (2013.01); *G01N 33/442* (2013.01)

(58) Field of Classification Search
CPC ...... G01N 21/94; G01N 1/2813; G01N 21/65; G01N 23/2251; G01N 33/442
See application file for complete search history.

(56) References Cited

PUBLICATIONS

Beach, E., et al., "Cross-sectional Analysis of Hollow Latex Particles by Focused Ion Beam-Scanning Electron Microscopy," Polymer Communication 46(2005): 11195-11197, Oct. 6, 2005.
(Continued)

*Primary Examiner* — Nicole M Ippolito
*Assistant Examiner* — Hanway Chang
(74) *Attorney, Agent, or Firm* — CHRISTENSEN O'CONNOR JOHNSON KINDNESS PLLC

(57) ABSTRACT

The present invention relates to a method for the detection of at least one nano or micro plastic particle comprised in a heterogeneous matrix material comprising the following steps: applying of at least one part of a heterogeneous matrix material comprising at least one nano or micro plastic particle onto at least a portion of a surface of a conductive support thereby forming a first layer onto said surface, irradiating of at least a portion of said first layer with at least one ion beam, thereby forming an irradiated layer, detecting of the at least one nano or micro plastic particle comprised in said irradiated layer by a detection method chosen from the group of Raman nanoscopic techniques, or infrared nanoscopic techniques, or charge dependent detection methods or combination thereof. The present invention allowed (Continued)

good detection of micro and nano plastic particles with high resolution and sensitivity.

20 Claims, 12 Drawing Sheets

(51) Int. Cl.
*G01N 21/65* (2006.01)
*G01N 23/2251* (2018.01)
*G01N 33/44* (2006.01)

(56) References Cited

PUBLICATIONS

Ding, J., et al., "Detection of Microplastics in Local Marine Organisms Using a Multi-Technology System," Analytical Methods, 11: 78-87, Nov. 12, 2018.

Wagner, J., et al., "Novel Method for the Extraction and Identification of Microplastics in Ocean Trawl and Fish Gut Matrices," Analytic Methods, 9: 1479-1490, Oct. 26, 2016.

Mai, L., et al., "A Review of Methods for Measuring Microplastics in Aquatic Environments," Environmental Science and Pollution Research, 25:11319-11332, Mar. 13, 2018.

International Search Report and Written Opinion dated Jun. 8, 2020, issued in corresponding International Application No. PCT/EP2020/052309 filed Jan. 30, 2020.

Extended European Search Report dated Mar. 28, 2019, issued in corresponding European Application No. EP19154521 filed Jan. 30, 2019.

METHOD FOR THE DETECTION AND QUANTIFICATION OF NANO OR MICRO PLASTIC PARTICLES

CROSS-REFERENCES TO RELATED APPLICATIONS

This application is a national phase entry of and claims priority to international patent application PCT/EP2020/052309, entitled "A METHOD FOR THE DETECTION AND QUANTIFICATION OF NANO OR MICRO PLASTIC PARTICLES," filed on Jan. 30, 2020, and further claims priority to European patent application EP19154521.9, entitled "A METHOD FOR THE DETECTION AND QUANTIFICATION OF NANO OR MICRO PLASTIC PARTICLES," filed on Jan. 30, 2019, the contents of both of which are hereby incorporated by reference in their entirety.

FIELD OF THE INVENTION

The present invention is in the field of analytical sciences, more specifically in the field of contaminants detection and quantification.

BACKGROUND

Since the 1950's which coincides with the beginning of large-scale production of plastics, the global production of plastics has steadily increased to even reach the 299 million tons mark in 2013. The considerable commercial success of plastics is due to a variety of reasons such as their ease of manufacture, low costs, their chemical and temperature resistance and mechanical properties. Nowadays, plastics are used in a wide variety of everyday products.

Since beginning 2000, concerns were raised regarding the pollution that plastic products can generate in the forms of microplastics and nanoplastics and its impact on wild life and human health. Microplastics and nanoplastics pollution arises for example from the breakdown of larger plastic items due to the wear and tear of plastic items exposed to the elements. Moreover, other degradation processes due to UV irradiation and microbiological activity are likely accelerating the breakdown of larger plastics (J. P. da Costa et al., Science of the Total Environment, Volume 566-567, 2016, pages 15-16). Moreover, nanoplastics and microplastics are sometimes deliberately added to the formulation of consumer products such as cosmetics, theses nanoplastics easily end up being dispersed in the environment.

J. P. da Costa et al. also reviewed the biological effects of nanoplastics and microplastics have already been demonstrated in the scientific literature. For instance, PS nanoparticles have been shown to be toxic towards macrophages and epithelial cells and can have an influence on cell viability, inflammatory gene expression and cell morphology.

Other toxicological risks can arise from the fact that organic pollutants tend to adsorb onto nanoplastics and microplastics due to their very high area-to-volume ratio. Therefore, if nanoplastics are ingested, it is possible that the adsorbed pollutants could leach into tissues.

A tremendous amount of analytical techniques were developed in order to try to detect or quantify microplastics and nanoplastics (Renner et al. Current Opinion in Environmental Science & Health, Volume 1, February 2018, Pages 55-61). Generally, when complex samples are to be analyzed, such as food samples or samples taken from the environment, nanoplastics and microplastics are most likely embedded into other materials. Thus, in order to be able to detect nanoplastics and microplastics, tedious purification and separation procedures are required in order to prepare the sample before analysis.

These purification procedure are based on density separation and (bio)chemical treatments. The latter are used to induce digestion of non-plastics and are usually able to conserve, at least partially, microplastics. The digestion usually require the use of strong acids, bases or hydrogen peroxides and may in some cases have adverse effect on the treated samples. For example, Dehaut et al. tested several digestion treatments of seafood samples containing microplastics having a size greater than 500 µm. Their results show that treatment with $HNO_3$, NaOH and KOH can induce degradation of some microplastics and should therefore be avoided. Moreover, depending on the sample, extra bones removal steps or modified filtration steps were necessary.

Courtene-Jones et al. (Courtene-Jones et al., Anal. Methods, The Royal Society of Chemistry 2017, 9, 1437) have developed a technique for detection of micro plastic particles in blue mussels using enzymatic digestion. The technique involves digestion of the micro plastics with proteolytic digestive enzymes such as trypsin, papain or collagenase and analysis with ATR-FTIR spectroscopy. The method has only been proven for micro plastic particles.

Rennie et al. studied microplastics contamination in Lake Winnipeg via scanning electron microscopy (SEM) and Energy Dispersive X-ray Spectroscopy (EDS). After being collected, the samples were subjected to a series of steps including: filtration through a 250 µm mesh brass sieve, rinsing with deionized water and digestion with a peroxide oxidation (WPO) treatment. Then, the microplastic particles were transferred to ethanol. Later, between 8 and 32 particles were chosen at random and placed on double-sided carbon tape, coated with a thin film of evaporated carbon under vacuum for SEM and EDS analysis. As Rennie et al. noted, the analyzed particles were smaller than 5 mm and typically larger than 333 µm in at least one dimension, moreover the rinsing step may have resulted in some losses of strongly-attached plastic particles.

There is thus a need to avoid chemical pretreatment of the sample to be analyzed since these are tedious and time consuming, due to the amount of steps to be carried out (bones removal step, digestion, filtrations). Moreover, the use of corrosive chemicals such as KOH, $HNO_3$ or NaOH is dangerous and can lead to microplastics degradation. Microplastics degradation must be avoided otherwise it will negatively impact the detection of microplastics in the sample.

Moreover, a main issue is to be able to detect, quantify and identify micro or nano plastic particle with a versatile method. Indeed, many techniques fail to do so because of their low resolution and sensitivity.

SUMMARY

The present invention relates to a method for the detection of at least one nano or micro plastic particle comprised in a heterogeneous matrix material comprising the following steps:
 a) applying of at least one part of the heterogeneous matrix material comprising the at least one nano or micro plastic particle onto at least a portion of a surface of a conductive support thereby forming a first layer (L1) onto said surface, said first layer (L1) having an average thickness equal to or lower than 10 µm, b) irradiating of at least a portion of said first layer (L1) with at least one ion beam, thereby forming an irradiated layer (L2), c) detecting of the at least one nano or micro plastic particle comprised in said irradiated layer (L2) as formed in step b) by a detection method chosen from the group of a mass spectroscopic technique, or a Raman nanoscopic technique, or an infrared nanoscopic technique, or a charge dependent detection method or a combination thereof.

DETAILED DESCRIPTION

Figure 1:
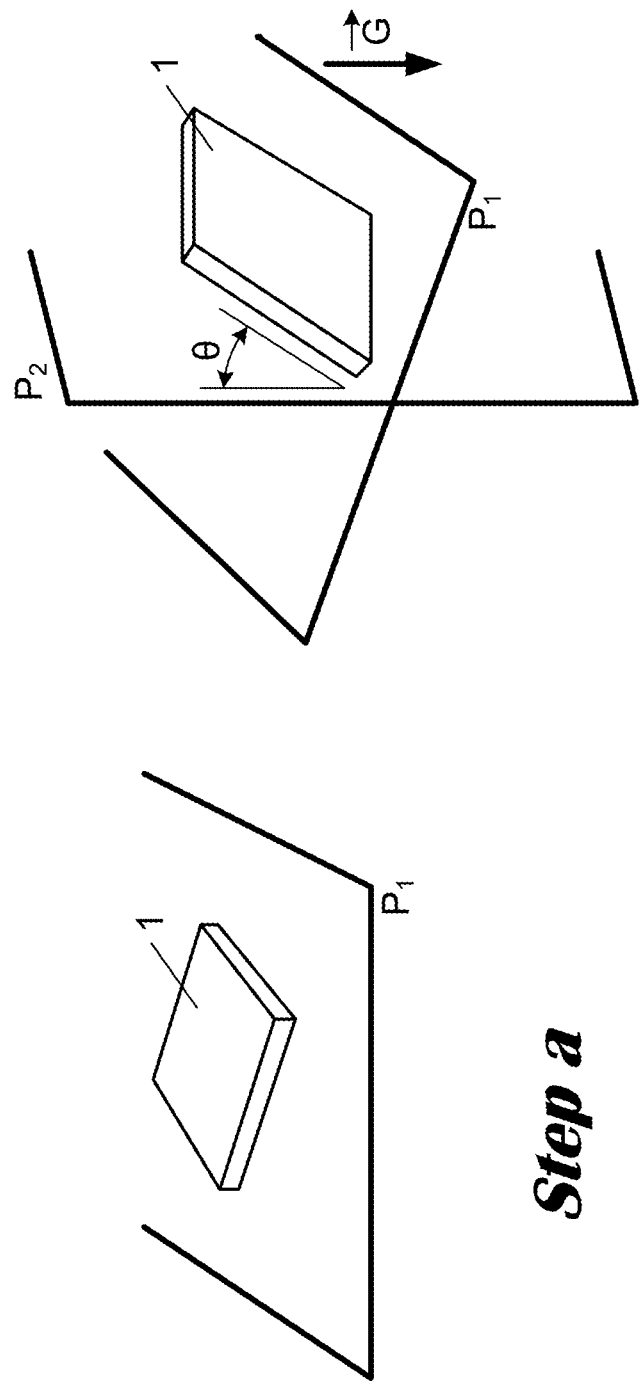
FIG. 1 is a schematic representation of an embodiment of the present invention in which a positioning step of the conductive substrate is carried out.

Within the context of the present invention, the expression "at least one nano or micro plastic particle" is intended to denote one or more nano or micro plastic particles.

In the context of the present invention, a micro plastic particle is intended to denote a plastic particle that is greater or equal than 1 μm and smaller than 1 mm in the largest of its dimensions and a nano plastic particle intended to denote a plastic particle that is smaller than 1 μm and greater than 1 nm in the largest of its dimensions.

The term "plastic" refers to any man-made polymer based material. Advantageously, a man-made polymer is a man-made thermoplastic polymer or a man-made thermoset polymer.

In the context of the present invention, the expression "heterogeneous matrix" is intended to denote a medium in which the at least one nano or micro plastic particle is embedded together with a substance or a mixture of substances. Said substances can be organic and inorganic, such as notably metals, biological substances and the like, in particular biological substances. It is further understood that biological substances refer to any dead or living organism or part thereof and any substance found within, purified from, or derived from any living organism or part thereof including notably cell membranes, nucleic acids, proteins, lipids, sugars and etc. Said living organism may be dead or alive. Non limitative examples of heterogeneous matrices notably include seafood, sediments, sea organisms, animals, plants and the like. In general, the heterogeneous matrix may further comprise water wherein the water may come from the environment, from running water or from a commercially available bottle of water. The medium may be in any form such as in the form of a liquid, a solution, a suspension, a paste, a cream, a solid, a tissue and the like.

The heterogeneous matrix may be a naturally occurring substance or may be a combination of synthetic, semi-synthetic and naturally occurring substances.

Illustrative examples of naturally occurring heterogeneous matrices include cell cultures grown on a surface, creams obtained from seafood, or cultures obtained by spreading-plating methods.

In the context of the invention, the "conductive support" is intended to refer to a support possessing sufficient electrical conductivity in order to allow irradiation by Focused Ion Beam, preferably by Focused metal ion beam, more preferably by Ga$^+$ focused ion beam.

Suitable conductive supports for providing excellent conductivity for example FIB are well known in the art. Advantageously, said conductive support is a wafer or a chip. In general, said wafer or chip is made of silicon, boron doped silicon, copper, nickel or combination thereof, preferably said wafer or chip is made of silicon.

Non-limiting examples of suitable conductive supports notably include silicon wafers, diced silicon wafers.

According to a preferred embodiment in the method of the present invention, said conductive support is rendered hydrophilic by plasma activation, UV activation or chemical activation.

In general, the conductive support has a top surface and a bottom surface. Advantageously, the at least one part of the heterogeneous matrix material comprising the at least one nano or micro plastic particle is applied onto at least a portion of the top surface of the conductive support.

According to one embodiment in the method of the present invention, at least part of the top and bottom surfaces of said conductive supports are substantially flat and parallel to one another.

According to an alternative embodiment in the method of the present invention, the top surface of the conductive support comprises at least a plurality of recesses having a width W and a depth D. Advantageously, the recesses have a cylindrical shape wherein said cylindrical shape is characterized by having a diameter W and depth D, both configured to receive at least the micro plastic particle, as detailed above or at least the nano plastic particle, as detailed above.

Advantageously, the distance L between the recesses is greater than the maximum resolution of the detection method, as detailed above, in particular of the Raman nanoscopic technique.

In the context of the invention, a "charge dependent detection method" is intended to refer to a method of detection which requires a conductive sample or gives improved results when the analysed sample is conductive. Preferably, the "charge dependent detection method" is an electron-based detection method, such as notably SEM, TEM, STEM, EDX or a combination thereof. More preferably, the charge dependent detection method is chosen from the group of SEM, EDX and combinations thereof.

The acronyms SEM refers to scanning electron microscopy, EDX refers to Energy Dispersive X-ray Spectroscopy, TEM refers to transmission Electron microscopy, STEM refers to scanning transmission electron microscopy.

An advantage of the method according to present invention is that it surprisingly allows a combination of several technical effects to occur. First of all, the irradiation step b) causes at least a partial or complete digestion of the heterogeneous matrix except for the nano and micro plastic particles comprised in this heterogeneous matrix. This being said, it is especially the biological substances including notably cell membranes, nucleic acids, proteins, lipids, sugars, etc which are at least partially removed from the first layer (L1) by the partial or complete digestion of the heterogeneous matrix. This has the beneficial effect of improving the detection of nano and micro plastic particles by the detection method according to step c). In general, prior to irradiation, some of the nano and micro plastic particles can be deeply embedded inside the heterogeneous matrix due to the fact that the nano and micro plastic particles are partially or even fully surrounded by the other substances, in particular biological substances. This renders their detection difficult or sometimes impossible. Upon irradiation according to step b), because of the partial or complete digestion of the heterogeneous matrix, the nano and micro plastic particles thereby being less surrounded by the other substances, in particular biological substances, are more available for detection according to step c), as detailed above.

At the same time, the at least one nano or micro plastic particle comprised in the irradiated layer (L2) as formed in step b) has an increased conductivity due to the implantation or incorporation of ions in step b) of the method of the present invention. This ions implantation increases the conductivity of the irradiated layer (L2). When the charge dependent detection method is used in step c) of the method of the present invention then this increased conductivity of the irradiated layer (L2) also allows an easier and better detection of the at least one nano or micro plastic particle. For example, SEM imaging of a non-conductive or a poorly conductive sample will give rise to a charging effect. The charging effect can generate artefacts during imaging. It is therefore very advantageous to be able to increase the conductivity of the analysed sample. It generally improves the quality of the image obtained by SEM and thus the quality of the detection.

In particular, if a $Ga^+$ focused ion beam is used in step c) of the method of the present invention then the implanted Ga ions can also act as contrast agents for charge dependent detection methods. For example, when the charge dependent detection method is SEM, the implanted ions increase the contrast of the obtained image. Indeed, the implanted nano and micro plastic particles appear very bright while the rest of the analysed area appears dark. Moreover, if the heterogeneous matrix contains at least a metal particle before said irradiation step c), it was observed that the irradiated ions are reflected on the metal particle present in the matrix.

Thanks to the combination of the abovementioned technical effects, it was surprisingly found out that the method according to the present invention allows good detection of micro and nano plastic particles with high resolution and sensitivity.

The average thickness can be measured using, for example, transmission electron microscopy (TEM), X-ray reflectivity (XRR), or x-ray photoelectron spectroscopy (XPS). The average thickness can be determined using calibration from standard samples having known thicknesses, for example.

Advantageously, the first layer (L1) has an average thickness of equal to or lower than 8 µm, more preferably equal to or lower than 6 µm, more preferably equal to or lower than 4 µm, more preferably equal to or lower than 2 µm, more preferably equal to or lower than 1 µm.

As per the lower limit of the average thickness of the first layer (L1), this is not particularly limited, provided that said first layer (L1) can still provide a good detection of the at least one nano or micro plastic particle comprised in the heterogeneous matrix with high resolution and sensitivity.

In general, the lower limit of the average thickness of first layer (L1) is determined by the choice of the manufacturing method of said first layer (L1), as discussed in detail below. Depending on the choice of the manufacturing method, the minimum thickness of the first layer (L1) can vary from 100 nm up to 500 µm.

In step (a) of the method of the present invention, the first layer (L1) can be formed by applying at least one part of the heterogeneous matrix material comprising the at least one nano or micro plastic particle onto at least a portion of the surface of the conductive support by using deposition techniques known in the art those including notably deposition coating methods, gluing methods, and the like.

Among coating methods mention may be notably made of drop-coating, spin-coating, spray coating, dip-coating and the like.

In general, the conductive support is placed substantially parallel to a first horizontal plane (P1) when the heterogeneous matrix material is applied in step a) onto at least a portion of the surface of the conductive support.

It is further understood that when the heterogeneous matrix material is in the form of a liquid, a solution, a suspension, a paste, or a cream that the method of the present invention further comprises a step of drying.

Preferably, the drying step is performed prior to the irradiation step b). This being said, the first layer (L1) is preferably a dried layer.

The method of drying is not specifically limited, but non limiting examples include dry air drying, hot air (warm air) drying and (far) infrared drying.

Advantageously, the drying step is carried out at a temperature below the glass transition temperatures (Tg) of the at least one nano or micro plastic particle in order to prevent modifying their structure but at a temperature high enough to assure efficient drying.

According to certain embodiments of the present invention, the drying step is carried out at a temperature between 20° C. and 100° C., or between 30° C. and 80° C., or between 30° C. and 70° C., or between 30° C. and 50° C.

Preferably, prior or during the drying step, the conductive support is positioned from being substantially parallel to a first horizontal plane (P1) to an angle ranging from +60° to −60°, preferably ranging from +45° to −45°, preferably ranging from +30° to −30°, more preferably ranging from +15° to −15° relative to a second vertical plane (P2), even more preferably substantially parallel to a second vertical plane (P2).

If desired, additional capillary forces can be applied on the first layer (L1) while being positioned substantially parallel to a first horizontal plane (P1) or while being tilted to an angle ranging from +60° to −60°, preferably ranging from +45° to −45°, preferably ranging from +30° to −30°, more preferably ranging from +15° to −15° relative to a second vertical plane (P2), even more preferably substantially parallel to a second vertical plane (P2), as detailed above, by using known techniques in the art. For example, the first layer (L1) is subjected to pressurization using a flat substrate such as notably the flat surface of a spatula.

The Inventors have found that applying gravic forces or/and capillary forces, as detailed above, improves the sample preparation. Indeed, due to the particular position of the conductive support, one part of the support is lower than the other part of the support. The lowest part is called the bottom of the support and the highest part is called the top of the support. Due to this particular position, gradients of matrix and nano and micro plastic plastic particles are created because of the combined actions of gravity and capillary forces. The concentration of nano and micro plastic particles relative to the total concentration of the heterogeneous matrix material is higher on top of the support than on the bottom of the support. The Inventors have further found that this has the beneficial effect that the nano and micro plastic particles located on the top part of the support are more easily detected during the detection step c) of the method according to the present invention.

Preferably, said surface of the conductive support presents an area between 0.5 cm$^2$ and 3 cm$^2$, more preferably between 0.5 cm$^2$ and 2 cm$^2$, even more preferably between 0.75 cm$^2$ and 1.5 cm$^2$.

As said, in the irradiation step b) of the method according to the present invention, at least a portion of the first layer (L1), as detailed above, is irradiated with at least one ion beam, thereby forming an irradiated layer (L2).

Advantageously, the at least one portion of said first layer (L1) possesses an area comprised between 2000 µm$^2$ and 500 µm$^2$, preferably between 1500 µm$^2$ and 800 µm$^2$, even more preferably between 1100 µm$^2$ and 800 µm$^2$.

According to a preferred embodiment of the method of the present invention, the first layer (L1) is irradiated by using a focused Ion beam (FIB) system, preferably by using a Ga$^+$ focused ion beam which are well known in the art.

It is generally known that the interaction of the ion beam with the ions with the first layer (L1) causes ion implantation and the first layer (L1) will be altered due to the sputtering effect. This depends on the irradiation dose used.

According to one embodiment of the method of the present invention, the radiation dose varies from $1*10^{13}$ to below $1*10^{17}$ ions/cm$^2$, preferably from $1*10^{15}$ to below $1*10^{17}$ ions/cm$^2$.

Using these doses of irradiation provides the partial or complete digestion of the heterogeneous matrix and ion implantation without transformation of the micro or nano plastic particles into amorphous carbon. The so obtained irradiated layer (L2) can then be subjected to any Raman or infrared based nanoscopic techniques (i.e. step (c) of the method) in order to identify the nature of the nano and micro plastic particles comprised in said irradiated layer (L2). Further, the so obtained irradiated layer (L2) can also be subjected to charge dependent detection methods, in particular SEM imaging (i.e. step (c) of the method) in order to allow easy detection of the nano and micro plastic particles.

According to another embodiment of the method of the present invention, the radiation dose varies from above $1*10^{17}$ to $1*10^{20}$ ions/cm$^2$, preferably from above $1*10^{18}$ to below $5*10^{19}$ ions/cm$^2$, more preferably from above $5*10^{18}$ to below $5*10^{19}$ ions/cm$^2$. In particular, an irradiation dose of $2*10^{19}$ ions/cm$^2$ is preferred.

Using these doses of irradiation provides the complete digestion of the heterogeneous matrix and ion implantation with transformation of the micro or nano plastic particles into amorphous carbon. The so obtained irradiated layer (L2) can then be subjected to any Raman, in particular confocal Raman Spectroscopy or infrared based nanoscopic techniques (i.e. step (c) of the method) in order to allow easy detection of the nano and micro plastic particles. Further, the so obtained irradiated layer (L2) can also be subjected to charge dependent detection methods, in particular SEM imaging (i.e. step (c) of the method) in order to allow easy detection of the nano and micro plastic particles.

This provides a way to discriminate between the at least one micro and nano plastic particle and the rest of the matrix. Hence, the detection of the least one micro or nano plastic particle is easily achieved.

As said above, the at least one nano or micro plastic particle comprised in the irradiated layer (L2) as formed in step b) are less surrounded by the other substances, in particular biological substances, and have an increased conductivity, all due to the implantation or incorporation of ions in step b) of the method of the present invention. This also allows as well an improved quantification of the at least one micro or nano plastic particles comprised in the irradiated layer (L2) as formed in step b).

When the nano and micro plastic particles are less surrounded by the other substances, in particular biological substances or even no longer covered by the biological substances then it is possible to quantify more correctly said nano and micro plastic particles.

As said above, the increased conductivity of the at least one nano or micro plastic particle reduces the risks of occurrence of charging effects. The artifacts resulting from charging effects can cause incorrect quantification of nano and micro plastic particles.

Typically, in the prior art when SEM is used as a charge dependent detection method, an electron energy higher than 10-15 KeV is used in order to allow good detection of metallic nanoparticles embedded in a heterogeneous matrix. In the present invention, particularly when irradiation doses as specified above are used, good quality imaging with good contrast between the irradiated micro and nanoplastic particles and the rest of the irradiated layer can still be obtained by using SEM with an electron acceleration voltage lower than 10 KeV, more preferably lower than 7 Key. Good results were obtained by using SEM with an electron acceleration voltage of about 5 KeV. Moreover, such low voltage reduces the risk of charging effect occurrence.

Advantageously, the method according to the present invention further comprises a step (d) of quantifying the at least one nano or micro plastic particle comprised in the irradiated layer (L2) as formed in step b) by using a mass spectroscopic technique, or a Raman nanoscopic technique, or an infrared nanoscopic technique, or a charge dependent detection method or a combination thereof, as detailed above.

According to one particular embodiment of the method of the present invention, the detection step (c) and the quantification step (d) of the micro plastic particles comprised in the irradiated layer (L2) as formed in step b) are carried out by using scanning electron microscopy (SEM).

According to another particular embodiment of the method of the present invention, the detection step (c) and the quantification step (d) of the nano plastic particles having a particle size of between 100 nm and 1000 nm in the largest of its dimensions comprised in the irradiated layer (L2) as formed in step b) are carried out by using energy dispersive X-ray spectroscopy (EDX).

The implanted ions also act as contrast agents when charge dependent detection methods are used during the quantification step (d). The contrast increase resulting from the irradiation step (b) according to present invention allows an easier and more correct quantification of nano and micro plastic particles. Indeed, poor contrast can cause some nano and micro plastic particles to be missed during quantification step.

Preferably, the Raman based nanoscopic technique is chosen from the group consisting of Confocal Raman spectroscopy, Tip Enhanced Raman Spectroscopy, and a combination thereof.

Preferably, said mass spectroscopic technique is TOF-SIMS (Time-of-Flight Secondary Ion Mass Spectrometry).

Preferably, the infrared based nanoscopic technique is nano Infrared Absorption spectroscopy.

Preferably, the Raman based nanoscopic technique is chosen from the group consisting of Confocal Raman spectroscopy, Tip Enhanced Raman Spectroscopy, and a combination thereof, or the infrared based nanoscopic technique is nano Infrared Absorption spectroscopy or the mass spectroscopic technique is TOF-SIMS.

The method according to the present invention may comprise for example a step of adding at least one particle of polystyrene of known size destined to be used as positive control to said heterogeneous matrix before step a) of applying of at least one part of the heterogeneous matrix. Preferably, said at least one particle of polystyrene has a size comprised between 10 and 2000 nm, even more preferably between 50 and 1000 nm.

Advantageously, the at least one micro or nano plastic particle is made of at least one polymer selected is from the group consisting of vinyl polymers, polyurethanes, polyesters, polyethers, polyamides, polyureas, polycarbonates, polydiene, conjugated polymers, copolymers and/or mixtures thereof.

Preferably, vinyl polymers are selected from the group constituted of acrylic polymers, polyolefins, polyvinyl acetals, polyvinyl esters, polyvinyl ethers, polyvinyl halides, polyvinyl ketones, styrene polymers, copolymers and/or thereof.

More preferably, said polyolefins are selected from the group constituted of polyethylene, polypropylene, copolymers and/or mixtures thereof.

More preferably, said acrylic polymers are selected from the group constituted of poly(acrylic acid), poly(methyl methacrylate), polyacrylonitrile poly(ethyl cyanoacrylate), polyacrylamide, copolymers and/or mixtures thereof.

Preferably, said conjugated polymers are selected from the group constituted of polyvinylenes, polyarylenevinylenes, polyarylenes, polyaryleneethynylenes, polydiacetylenes, copolymers and/or mixtures thereof.

Preferably, said polydiene are selected from the group constituted of polyisoprene, polybutadiene, polychloroprene, copolymers and/or mixtures thereof.

Even more preferably, the at least one micro or nano plastic particle is made of at least a polymer selected from the group consisting of polystyrene, polyethylene, polyethylene thereftalate, polypropylene, polyurethane, polyvinylchloride, polyester, polyacrylonitrile, polybutadiene styrene, polybutadiene acrylonitrile and mixtures thereof.

Even more preferably said at least one polymer is linear polymer or branched polymer or star polymer or at least partially crosslinked polymer or a mixture thereof.

FIG. 1 is a schematic representation of an embodiment of the present invention in which a positioning step of the conductive substrate is carried out.

After formation of the first layer (L1), a drying step is preferably performed. During or prior the drying step, the conductive support is substantially parallel to a first horizontal plane P1. Then, the conductive support is positioned so as to form an angle θ ranging from +60° to −60°, preferably ranging from +45° to −45°, preferably ranging from +30° to −30°, more preferably ranging from +15° to −15° relative to a second vertical plane P2, even more preferably substantially parallel to the second vertical plane P2.

Figure 2:
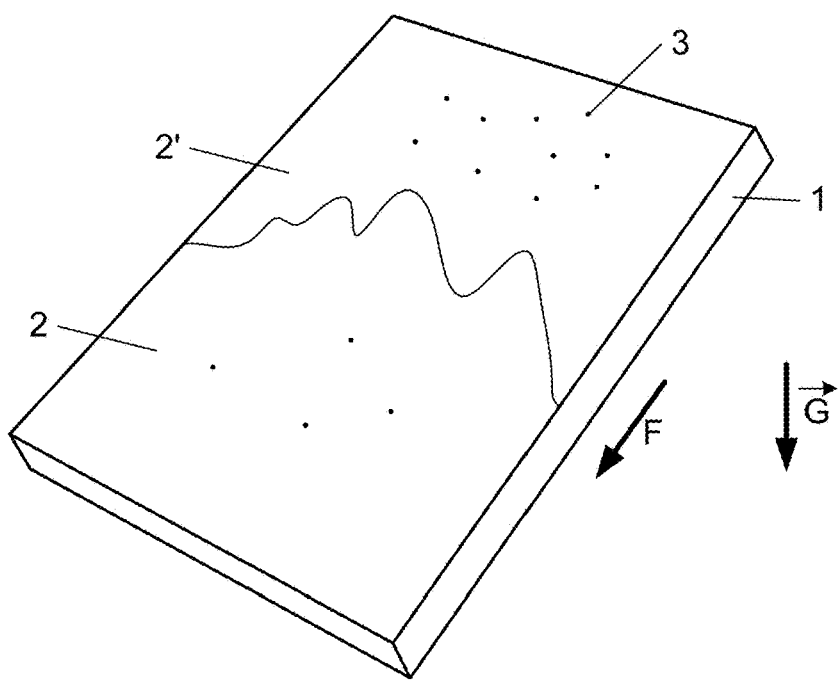
FIG. 2 is a representation of the support and said first layer (L 1) after the additional steps described in FIG. 1.

FIG. 2 is a representation of the support and said first layer (L1) after the additional steps described in FIG. 1.

The FIG. 2 shows the effect of the positioning step shown in FIG. 1 on the first layer (L1). Due to the position of the conductive support 1 resulting from said positioning step shown in FIG. 1, bottom part 2 of the support 1 is lower than the top part 2' of the support 1. Consequently, in the layer (L1), gradients of matrix and nano and micro plastic particles 3 are created because of the combined actions of gravity and capillary forces. The concentration of nano and micro plastic particles relative to the total concentration of the heterogeneous matrix material becomes higher on the top part 2' of the support than on the bottom part 2 of the support. As a result, the nano and micro plastic particles located on the top part 2' of the support are more easily detected than the nano and micro plastic particles located on the bottom part 2 of the conductive support 1 during the detection step c) of the method according to the present invention.

The invention will be now described in more details with reference to the following examples, whose purpose is merely illustrative and not intended to limit the scope of the invention.

EXAMPLE 1

This example is designed as a proof of concept in which polystyrene nanoparticles were deliberately added to a commercial juice in order to prove that the method according the present invention allows the detection and quantification of the added polystyrene nanoparticles.

1 ml of commercial tomato juice was mixed with 1 microliter of polystyrene nanoparticles having a concentration of 4% in water whereby said polystyrene nanoparticles have an average particle size of 200 nm. The obtained mixture was then diluted for 50% by adding ethanol. 20 microliters of the obtained diluted mixture was then applied by spin-coating on a 1 $cm^2$ silicon chip, previously made hydrophilic by plasma activation, thereby forming a first layer (L1) having an average thickness of 10 μm on the silicon ship. The spin coating was performed with a spin coating device at room temperature, at the speed of 2000 spins per minutes for 1 min under of a flow of air.

Then, the first layer was irradiated by Ga+ ions using FIB with an ion dose of $2*10^{19}$ ions/$cm^2$, an acceleration voltage of 30 keV for a period of 1 minutes, thereby forming an irradiated layer (L2).

Then a portion having an area of 50*50 $\mu m^2$ of the irradiated layer was visualized by SEM using secondary electron detection, 5 keV acceleration voltage and an aperture of 0.98 pA.

Figure 3:
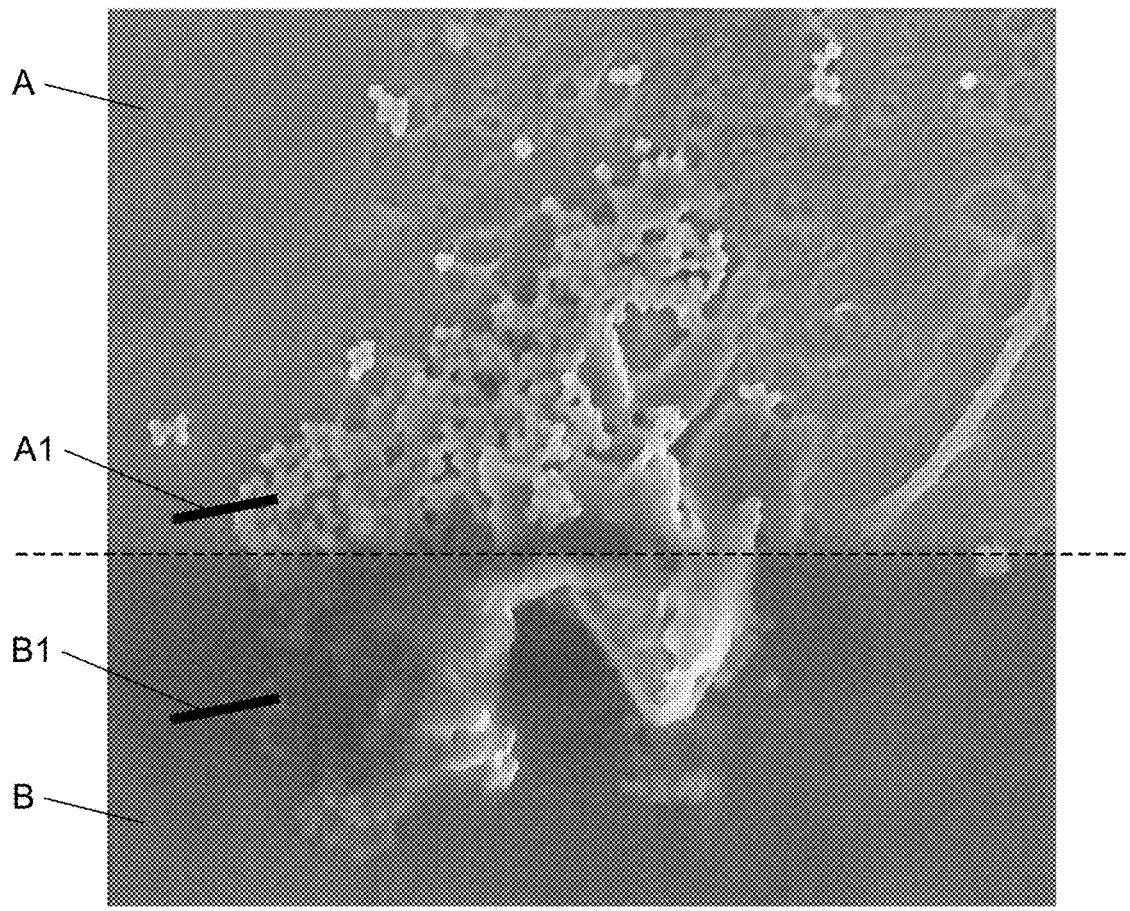
FIG. 3 shows a SEM image with a zone A that was irradiated with Ga+ ions and a zone B that was not irradiated.
Figure 4:
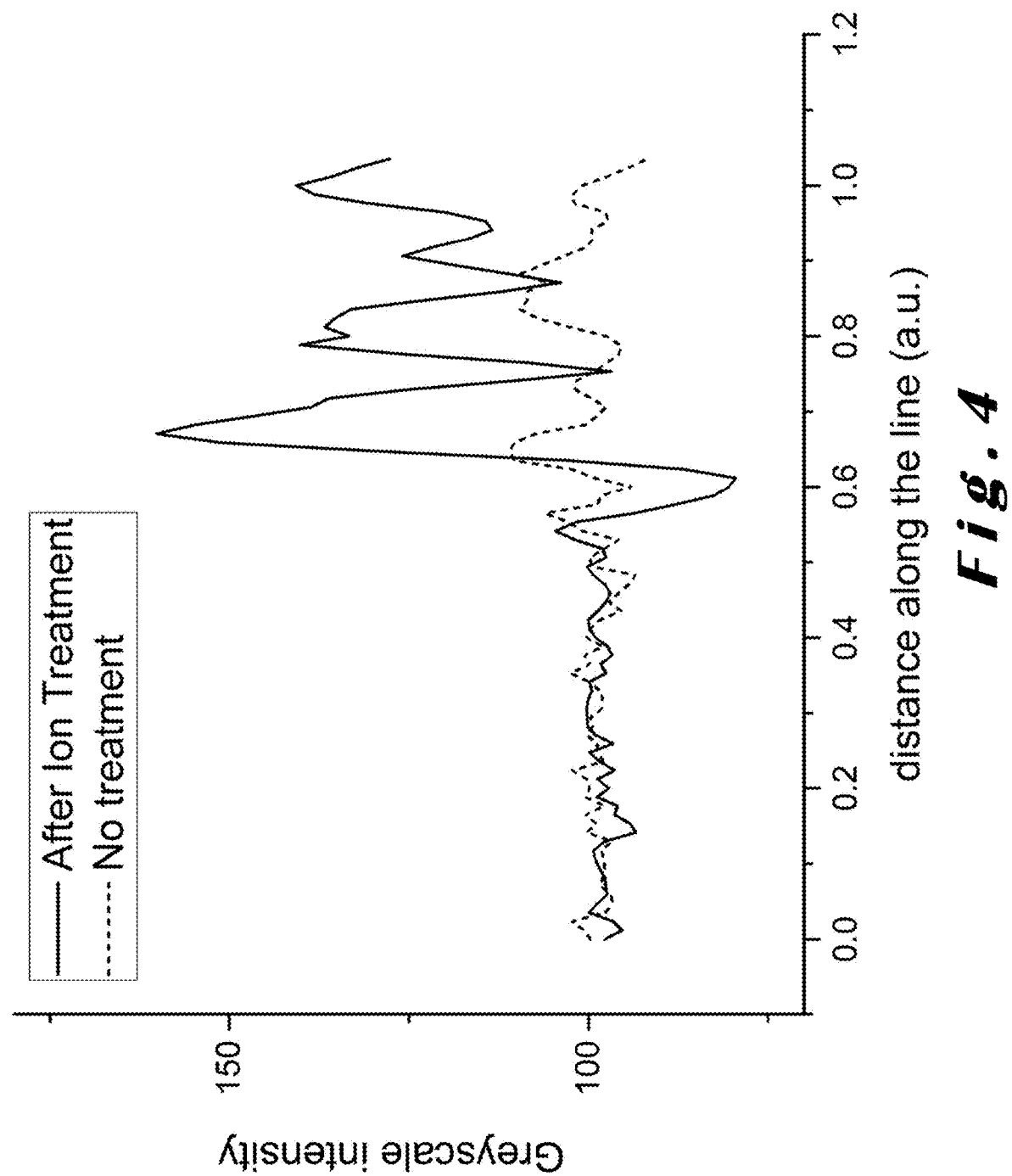
FIG. 4 shows the grey scale analysis along the lines A 1 et B 1.

The results are shown in FIGS. 3 and 4. FIG. 3 shows a SEM image with a zone A that was irradiated with Ga+ ions and a zone B that was not irradiated. As it can be clearly seen, in zone A, the contrast is improved and thus the polystyrene nanoparticles are clearly visible. To the contrary, in zone B, the contrast is not good and it is not easy to distinguish the polystyrene nanoparticles. FIG. 4 shows the grey scale analysis along the lines A1 et B1. The line A1 being in the zone A and the line B1 being in zone B. As we can see the grey scale varies more in the case of line A1 than in the case of line B1 when comparing the polystyrene nanoparticles to their surroundings, which confirms that the contrast is improved in zone A which was irradiated in comparison to zone B which was not irradiated.

This is due to a combination effects resulting from the FIB Ga+ irradiation. Firstly, in zone A the polystyrene nanoparticles appear more bright than in zone B and secondly, the heterogeneous matrix surrounded the polystyrene nanoparticles is greatly reduced in zone A in comparison to zone B. This confirms that FIB Ga+ irradiation improves nano and micro plastic particles detection via a combination of at least two effects: digestion of the heterogeneous matrix and implantation of Ga+ in the nano and micro plastic particles.

EXAMPLE 2

Figure 5:
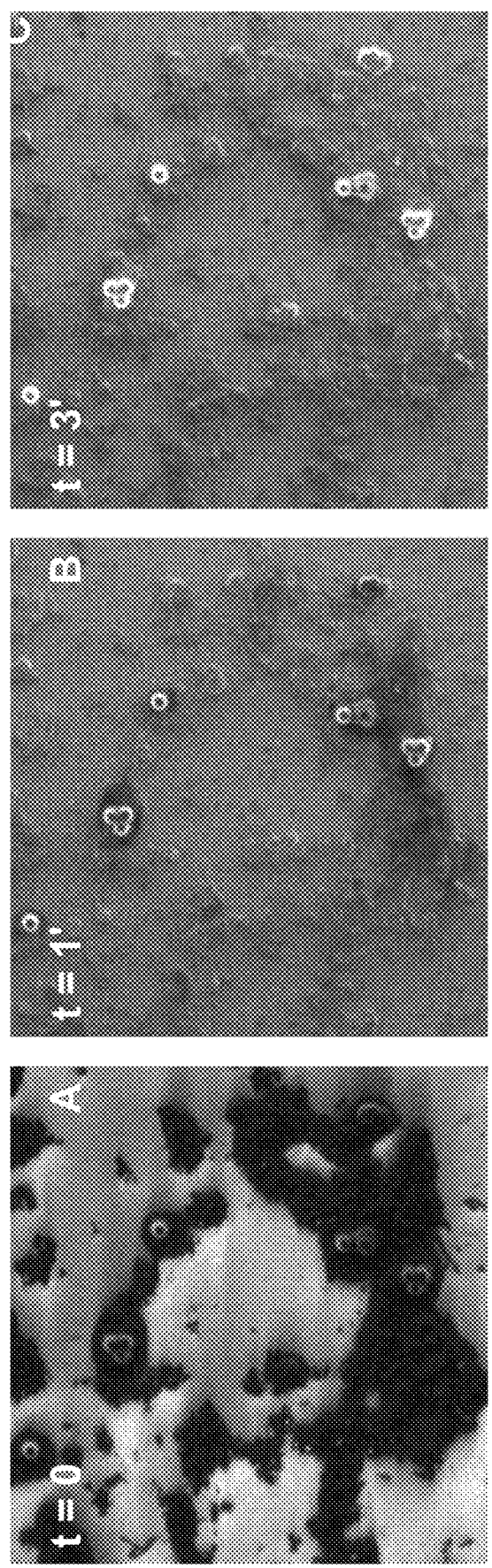
FIG. 5 contains three SEM images of the same area at different irradiation times.

1 ml of a sample containing a heterogeneous matrix of animal mussels in the form of a cream was mixed with 1 microliter of polystyrene nanoparticles having a concentration of 4% in water whereby said polystyrene nanoparticles have an average particle size of 200 nm.
The heterogeneous matrix is diluted in an equal volume of ultrapure water to obtain a diluted heterogeneous matrix. A portion of 20 microliters of the diluted heterogeneous matrix is then dropped on a 1 cm$^2$ silicon chip (previously made hydrophilic by plasma activation) so that it covers all the chip and forms a thin wet first layer presenting an average thickness of 10 μm.
The coated silicon ship was then placed in a vertical position and dried at 40° C. for 5 minutes.
Irradiation with Low Ion Dose
An area of 50*50 μm of the first layer located at the top of the ship was irradiated by Ga+ ions using FIB with an ion dose of 2*10$^{16}$ ions/cm$^2$, an acceleration voltage of 30 keV, 280 pA for a period of 1 minute, thereby forming an irradiated layer.
Then that area of 50*50 μm$^2$ of the irradiated layer was visualized by SEM using secondary electron detection, 5 keV acceleration voltage and an aperture of 0.98 pA.
The irradiated layer was also analysed by confocal Raman scanning. A good Raman spectrum could be obtained. The obtained spectrum allow the detection, quantification and the determination of the nature of nano and micro plastic particles.
Irradiation with High Ion Dose
Then, an area of 50*50 μm of the first layer located at the top of the ship was irradiated by Ga+ ions using FIB with an ion dose of 2*10$^{19}$ ions/cm$^2$, an acceleration voltage of 30 keV, 280 pA for a period of 1 minutes, thereby forming an irradiated layer.
Then that area of 50*50 μm$^2$ of the irradiated layer was visualized by SEM using secondary electron detection, 5 keV acceleration voltage and an aperture of 0.98 pA.
FIG. 5 contains three SEM images of the same area at different irradiation time. Image A was taken before irradiation, image B, was taken after 1 minute of irradiation and image C was taken after three minutes of irradiation. It is clear that the contrast increases with increasing irradiation time. The polystyrene nanoparticles become more bright with increasing irradiation time due to Ga+ ion implantation. Furthermore, the heterogeneous matrix surrounding the polystyrene nanoparticles is decreased due to sputtering. This confirms that FIB Ga+ irradiation improves nano and micro plastic particles detection via a combination of at least two effects: digestion of the heterogeneous matrix and implantation of Ga+ in the nano and micro plastic particles.

The irradiated layer was also analysed by confocal Raman scanning. Since only the nano and micro plastic particles and not those of the biological materials are converted to amorphous carbon, the Raman spectrum becomes the one of an amorphous carbon thereby allowing a direct way to discriminate between the micro and nano plastic particles and those related to biological materials.

EXAMPLE 3: DETECTION OF POLYMER NANOPARTICLES IN CELL MONOLAYERS

Figure 6:
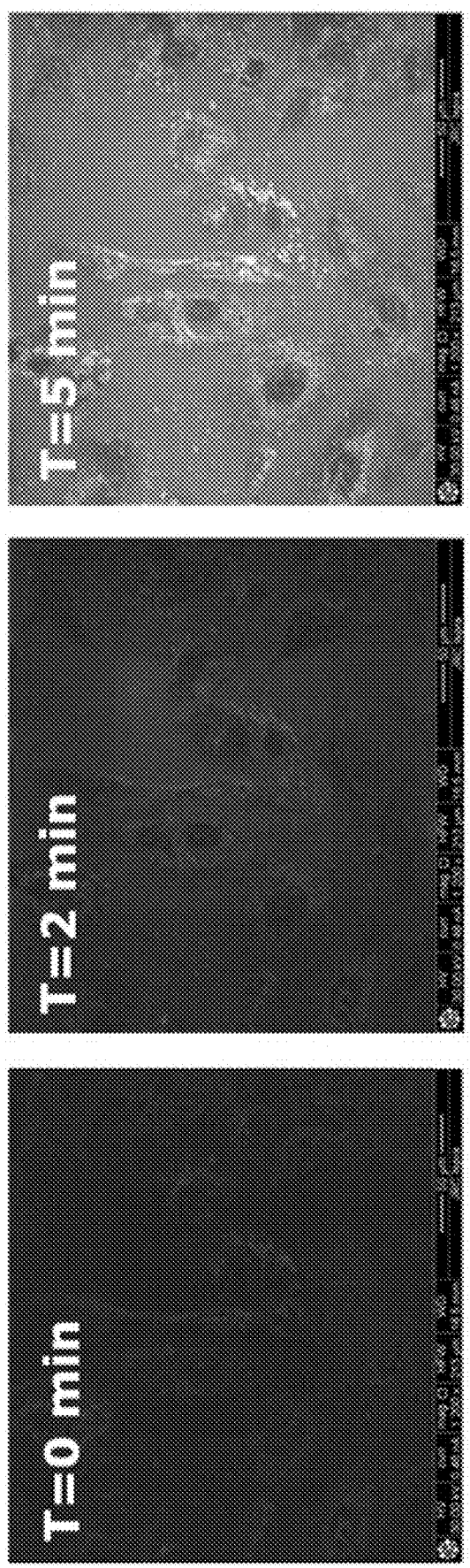
FIG. 6 contains three SEM images of the same area at different irradiation times.
Figure 7:
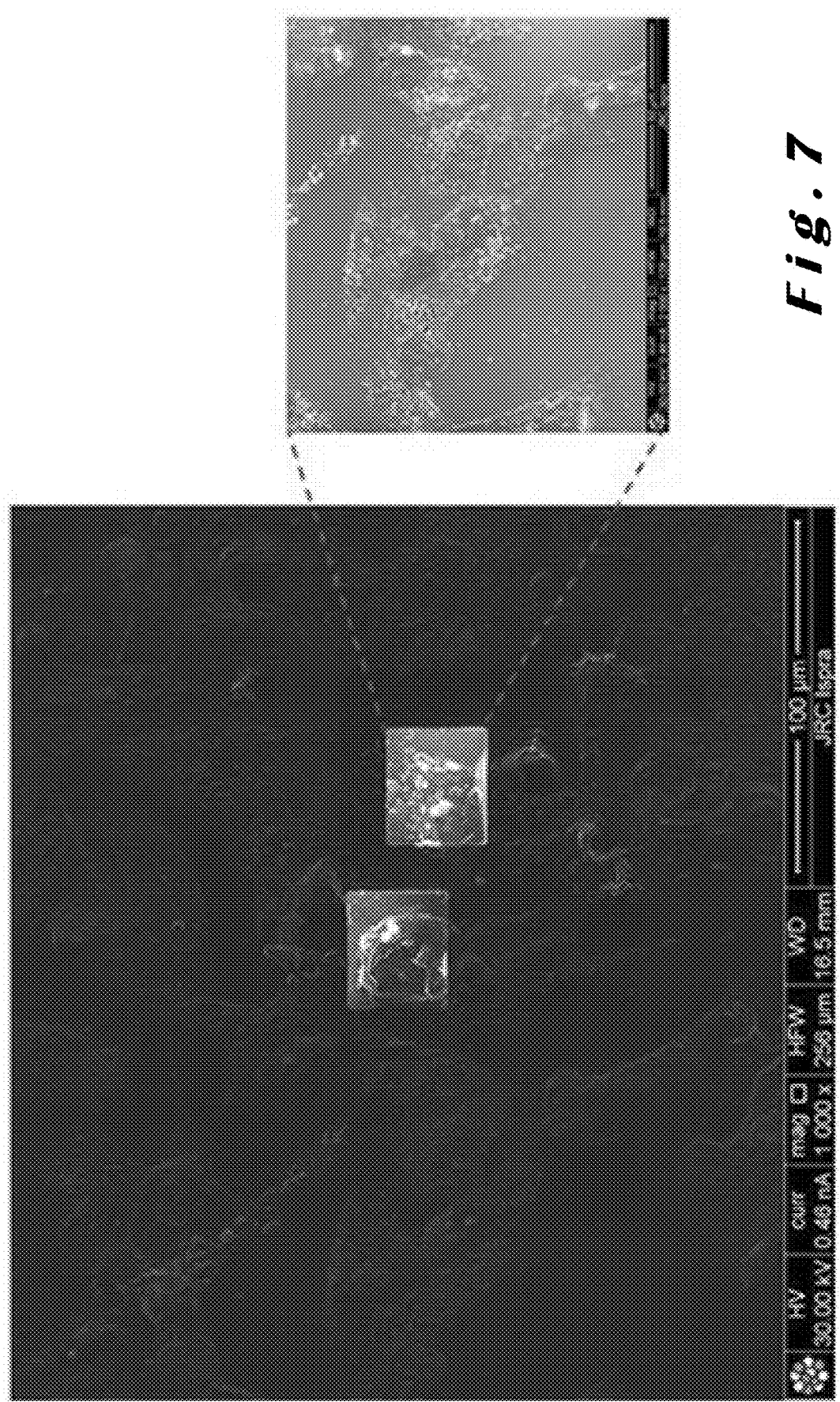
FIG. 7 shows irradiated areas showing polystyrene nanoparticles (NPs) inside the cells by the increased contrast between the nanoplastics and the heterogeneous matrix.

A 150-nm thick pAA layer was deposited on silicon wafer by plasma processing. The coated wafer was then cut in 10×10 mm chips, rinsed in ultrapure water and sterilized under UV light for 1 hour. After sterilization the chips were immersed in 1×PBS (Phosphate Buffered Saline) for 1 day in order to check the film stability. A549 cells (i.e. example 3A) or Balb 3T3 cells (i.e. example 3B) were seeded at a concentration of 50 000 cell/ml on 24 well plates containing the sterilized chips on the bottom. After 72 hours, the silicon chips containing A549 cells samples (i.e. example 3A) or Balb 3T3 cells samples (i.e. example 3B) were transferred to new 24 well plates and the cells were exposed to polystyrene beads of 200 nm diameter (PS-NPs, Polybead® Non-functionalized Microspheres (PS)—these particles contain a slight anionic charge from sulphate ester) for 3 days. Then, the A549 cells (i.e. example 3A) or Balb 3T3 cells (i.e. example 3B) were washed one time with PBS, fixed in 4% formaldehyde, washed three times with PBS, then with distilled water, and dehydrated in increasing concentrations (25, 50, 75 and 100%) of ethanol.
The so obtained A549 cells (i.e. example 3A) were irradiated by Ga+ ions using FIB with an ion dose of 2*10$^{19}$ ions/cm$^2$, an acceleration voltage of 30 keV for a period of 1 minute, thereby forming an irradiated layer (L2).
Then a portion having an area of 50*50 μm$^2$ of the irradiated layer was visualized by SEM using secondary electron detection, 5 keV acceleration voltage and an aperture of 0.98 pA.
FIG. 6 contains three SEM images of the same area at different irradiation time. Image A was taken before irradiation, image B, was taken after 2 minutes of irradiation and image C was taken after five minutes of irradiation. It is clear that the contrast increases with increasing irradiation time. The adherent A549 cells are straightforwardly recognizable on the sample as they have triangular or elongated shape with darker nuclei within the cell contour. The polystyrene nanoparticles become more bright with increasing irradiation time due to Ga+ ion implantation. Furthermore, the great majority of the heterogeneous matrix (cell membranes, nucleic acids, proteins, lipids, sugars, etc.) was digested by the ion beam for a selective sputtering effect as observed in FIG. 6. This confirms that FIB Ga+ irradiation improves nano and micro plastic particles detection via a combination of at least two effects: digestion of the heterogeneous matrix and implantation of Ga+ in the nano and micro plastic particles.
The so obtained Balb 3T3 cells (i.e. example 3B) were irradiated by Ga+ ions using FIB with an ion dose of 2*10$^{19}$ ions/cm$^2$, an acceleration voltage of 30 keV for a period of 1 minute, thereby forming an irradiated layer (L2).
Then a portion having an area of 50*50 μm$^2$ of the irradiated layer was visualized by SEM using secondary electron detection, 5 keV acceleration voltage and an aperture of 0.98 pA.
The result is shown in FIG. 7. The irradiated areas clearly show polystyrene nanoparticles (NPs) inside the cells by the increased contrast between the nanoplastics and the heterogeneous matrix. Furthermore, the great majority of the heterogeneous matrix (cell membranes, nucleic acids, proteins, lipids, sugars, etc.) was digested by the ion beam for a selective sputtering effect as observed in FIG. 7. This confirms that FIB Ga+ irradiation improves nano and micro plastic particles detection via a combination of at least two effects: digestion of the heterogeneous matrix and implantation of Ga+ in the nano and micro plastic particles.

EXAMPLE 4

1 ml of a sample containing a heterogeneous matrix of animal mussels in the form of a cream was mixed with 1 microliter of polystyrene nanoparticles having a concentration of 4% in water whereby said polystyrene nanoparticles have an average particle size of 1 μm.

The heterogeneous matrix was digested, and separated by centrifugation and filtration. Then it was drop coated onto a silicon conductive support comprising a plurality of recesses, having a cylindrical shape with a width W of 1 μm and depth D of 1 μm, and a distance L between the recesses is 2 μm, thereby forming a first layer (L1) which was dried. Due to capillary forces, some polystyrene nanoparticles having the proper particle size (i.e. equal to or lower than 1 μm) felled inside some recesses. Aggregated polystyrene nanoparticles which were trapped in the heterogeneous matrix did not fall into any of the recesses. This is demonstrated in FIG. 8.

Then, the first dried layer (L1) was irradiated by Ga+ ions using FIB with an ion dose of $2*10^{19}$ ions/cm$^2$, an acceleration voltage of 30 keV for a period of 1 minutes, thereby forming an irradiated layer (L2).

Then a portion having an area of 50*50 μm$^2$ of the irradiated layer was visualized by SEM using secondary electron detection, 5 keV acceleration voltage and an aperture of 0.98 pA.

Figure 9:
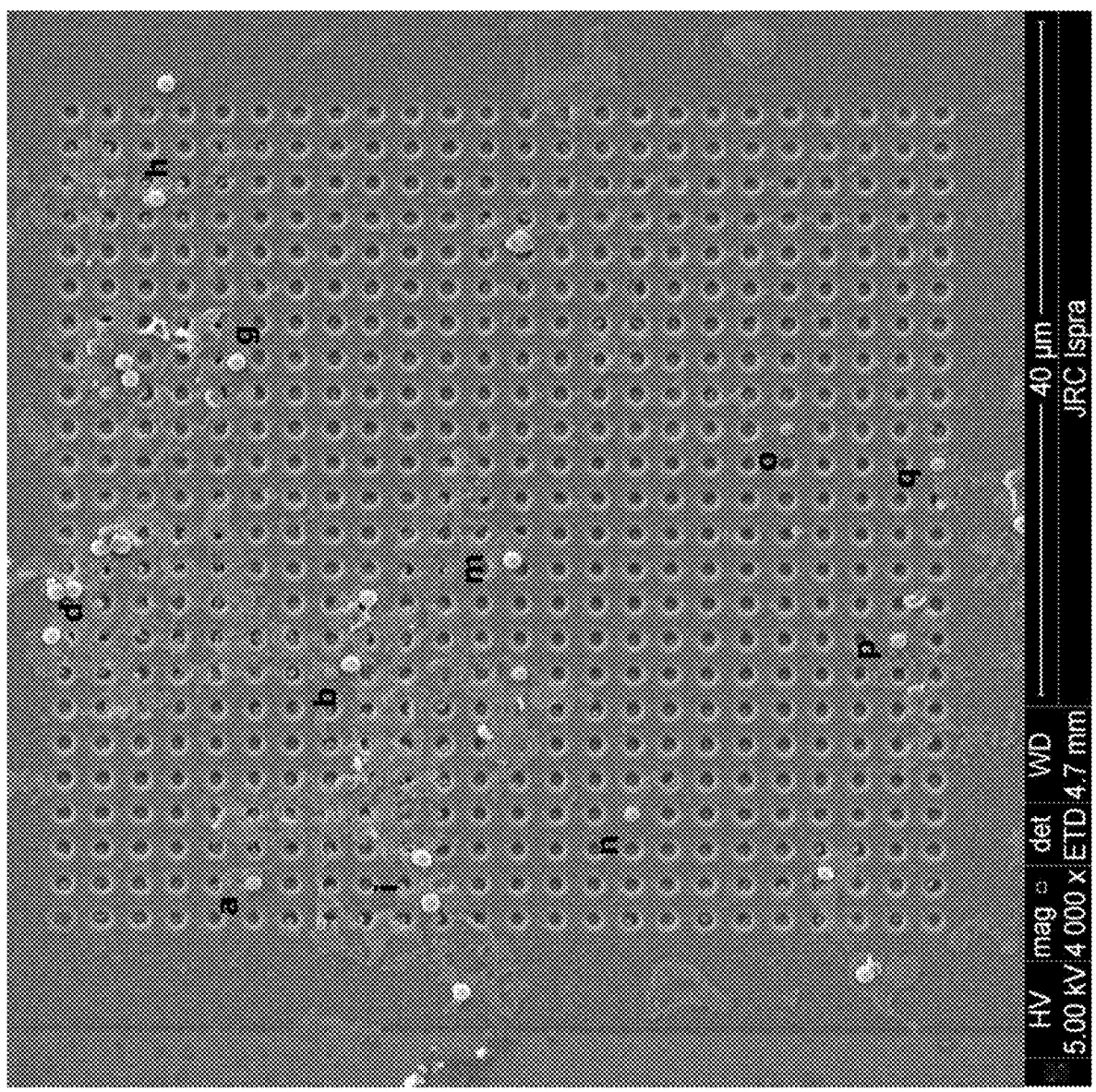
FIG. 9 is a SEM image where particles a, b, d, e, g, h, I, m, n, o, p, q can be seen.

The obtained SEM image is shown in FIG. 9 where particles a, b, d, e, g, h, i, m, n, o, p, q can be seen. As can be seen, for example particles a, b, n, o, p and q appear to have a lower contrast than particles g, h, d, i and m. It can also clearly be seen that particles g, h, d, i and m are not located inside a recess. As a result of the FIB Ga+ irradiation, the polystyrene nanoparticles outside the recesses are visible because they are characterized by a larger contrast compared to the polystyrene nanoparticles inside the recesses.

Figure 8:
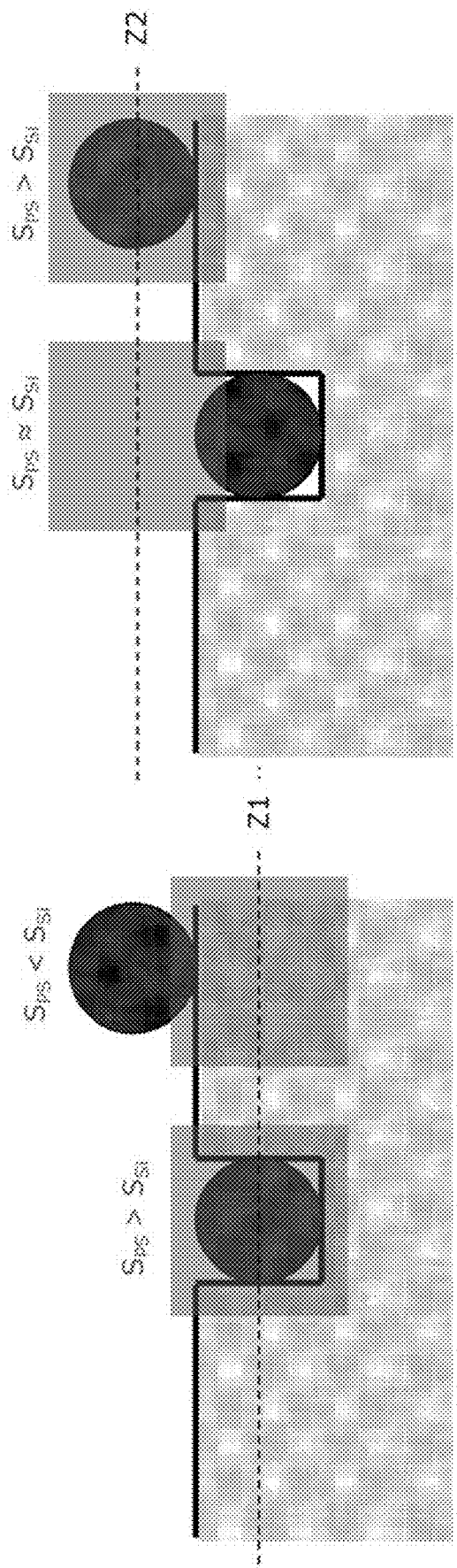
FIG. 8 shows aggregated polystyrene nanoparticles trapped in the heterogeneous matrix that did not fall into any of the recesses.

The irradiated layer (L2) was also analysed by Confocal Raman Scanning Microscopy. The scanning was performed at two different levels, level Z1=−1 μm and Z2=+2.5 μm in height relative to the height of the optical focus as shown in FIG. 8. A Raman spectrum per each pixel was acquired. A Raman spectrum was obtained for each position of the scanning. In this way 4-Dimensional hyperspectral data were created (with coordinates: x,y, wavenumber, Raman intensity). By proper univariate analysis (band integration), the hyperspectral data were reduced to 3 dimensional data (with coordinates x, y, Raman intensity). The obtained 3-D data are shown as black/white images where the bright spots correspond to positions where the intensity of the benzene vibration peak (typical of the Polystyrene) spectrally located at 1005 cm$^{-1}$ are larger than the one of the Silicon (2$^{nd}$ order peak) located at 960 cm$^{-1}$.

It has been demonstrated that it is possible to discriminate between particles inside the recesses and outside. In this way it is possible to filter the particles according to their size and characterize only the particles below a certain size, separating them from bigger particles.

Figure 10:
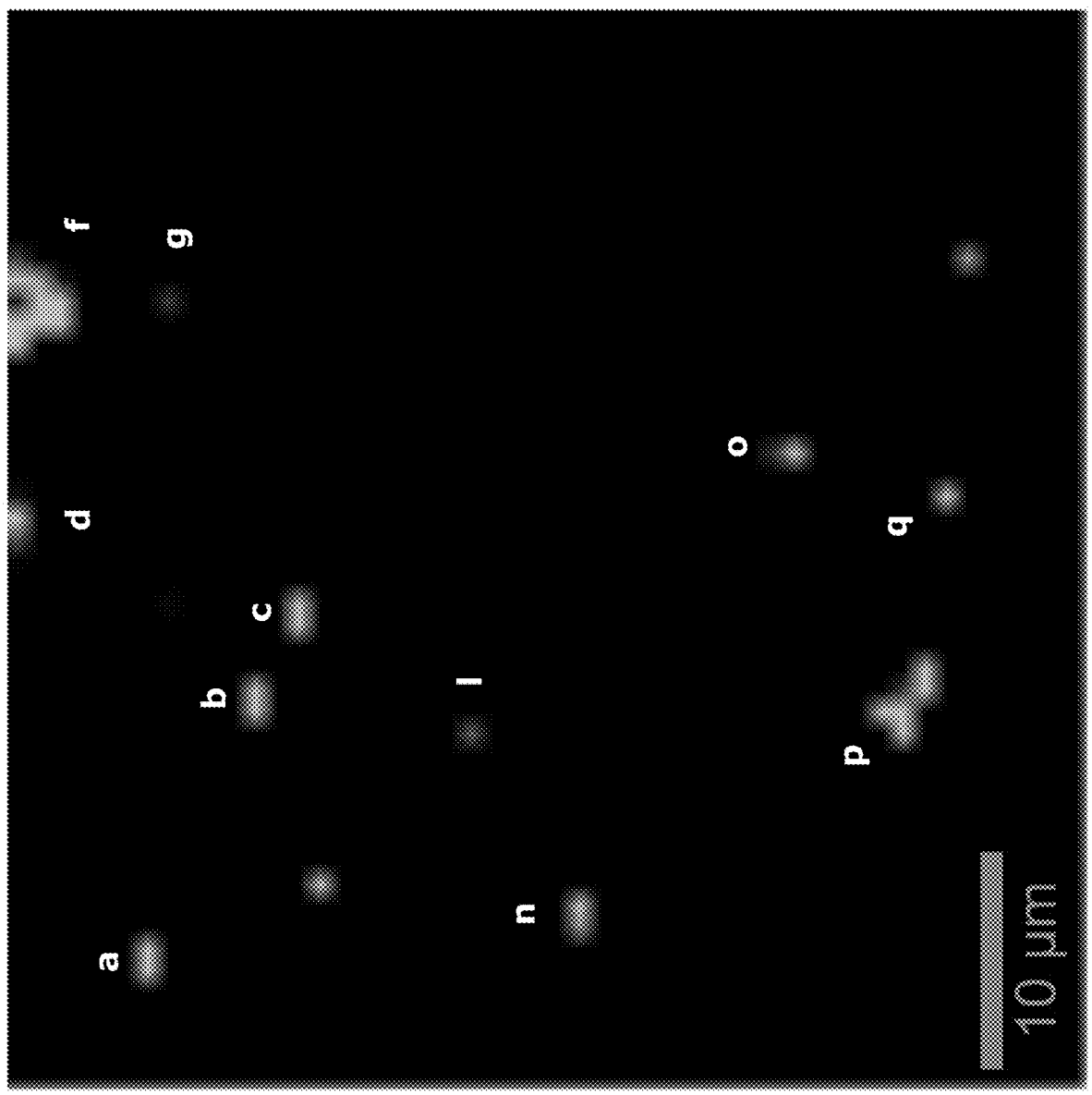
FIG. 10 is a map with the relative intensities when scanning is performed at the lower position (z=−1 μm).
Figure 11:
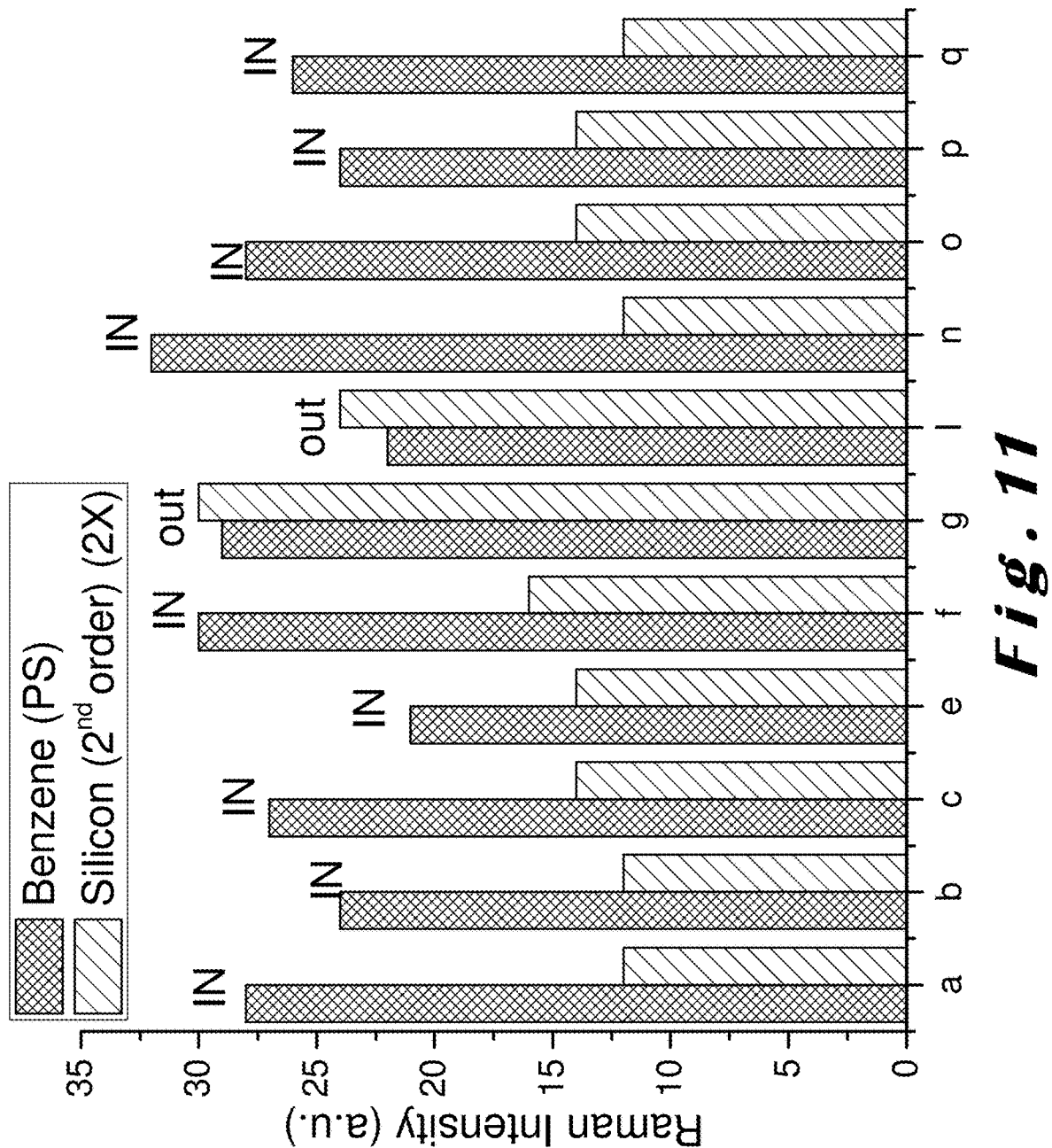
FIG. 11 is a comparison of the Raman intensities for some of the particles.

When the scanning is performed at the lower position (z=−1 μm) the intensity of the Raman peak the Benzene is more than double than the intensity of the Raman peak of the Silicon. Following this rule a map of the particles can be drawn and the particles inside the recesses can be evidenced. A map with the relative intensities when the scanning is performed at the lower position (z=−1 μm), is shown in FIG. 10. The bright spots correspond to the Raman peak of the benzene and thus to the polystyrene nanoparticles. By comparing FIGS. 10 and 11, it is possible to see that the particles inside the recesses such as particles a, b, n, o, p and q are detected by Confocal Raman Scanning Microscopy (FIG. 10). A comparison of the Raman intensities for some of the particles is also shown in FIG. 11. As can be seen, when the position is at z=−1 μm, the intensity of a benzene signal for particles located inside a recess is larger than the intensity of the corresponding Si signal (2$^{nd}$ order). However, when a particles outside a recess can be detected when the position is at z=−1 μm, the intensity of the benzene signal is lower or substantially equal to the intensity of the Si signal, as evidenced in the case of particle g for example.

Figure 12:
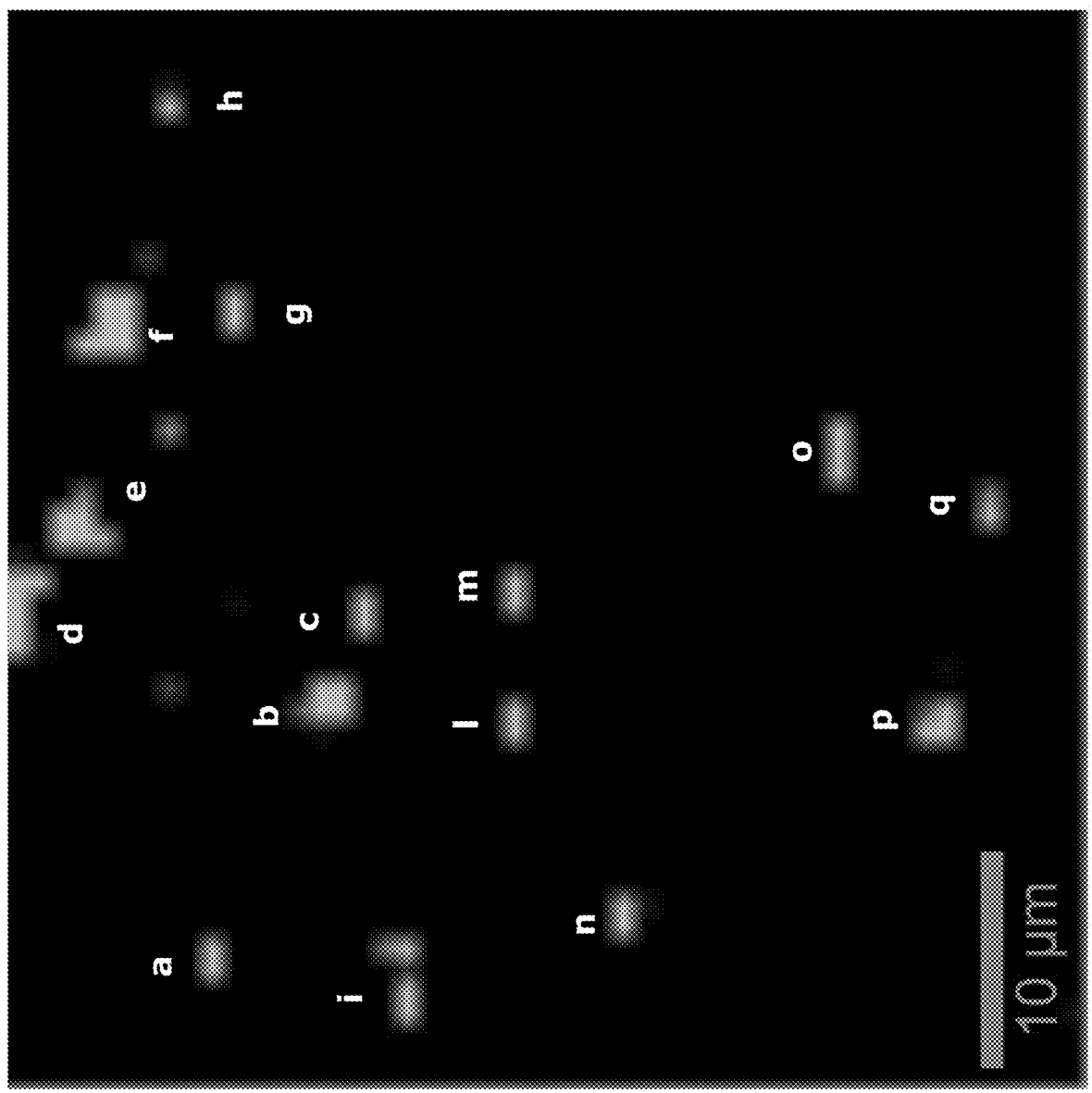
FIG. 12 represents a map with the relative intensities when the scanning is performed at a higher level than the level of the optical focus (z=+2.5 μm).
Figure 13:
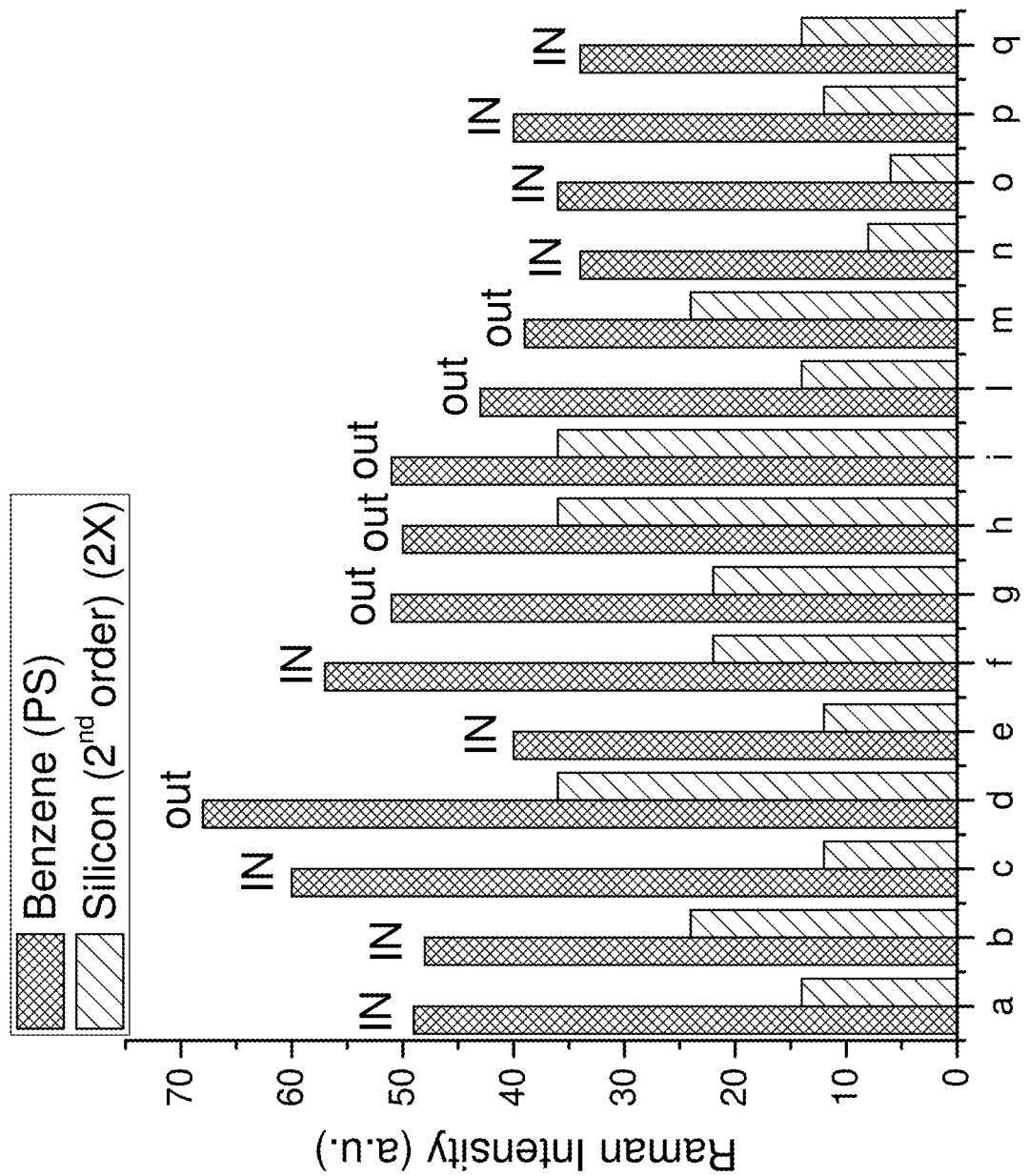
FIG. 13 shows a comparison of the Raman intensities for some of the particles shown in FIG. 12.

On the other hand, if the scanning is performed at a level higher than the level of the optical focus (z=+2.5 μm), more particles are detected, in particular all the particles detected. Indeed, in addition to the particles detected at a lower level such as z=−1 μm, the particles located outside the recesses are also detected. FIG. 12 represents a map with the relative intensities when the scanning is performed at a higher level than the level of the optical focus (z=+2.5 μm). As can be seen, particles a, b, c, d, e, f, g, h, i, I, m, n, o, p, q can be detected. FIG. 13 shows a comparison of the Raman intensities for some of the particles shown in FIG. 12.

The invention claimed is:

1. A method for the detection of at least one nano or micro plastic particle comprised in a heterogeneous matrix material comprising the following steps:
   a) applying of at least one part of a heterogeneous matrix material comprising the at least one nano or micro plastic particle onto at least a portion of a surface of a focused ion beam irradiable electrically conductive support thereby forming a first layer onto said surface, said first layer having an average thickness equal to or lower than 10 μm, the heterogeneous matrix being a medium in which the at least one nano or micro plastic particle is embedded together with a substance or a mixture of substances, the medium being selected from the group consisting of a liquid, a solution, a suspension, a paste, a cream, a tissue and wherein the heterogeneous matrix is a naturally occurring substance selected from the group consisting of cell cultures grown on a surface, creams obtained from seafood, and cultures obtained by spreading-plating methods;
   b) irradiating of at least a portion of said first layer with at least one ion beam, thereby forming an irradiated layer, the at least a portion of said first layer being irradiated by using a Ga$^+$ focused ion beam with a radiation dose which varies from $1*10^{13}$ to below $1*10^{17}$ ions/cm$^2$ or with a radiation dose which varies from above $1*10^{17}$ to $1*10^{20}$ ions/cm$^2$,
   c) detecting of the at least one nano or micro plastic particle comprised in said irradiated layer as formed in step b) by a detection method chosen from the group of a mass spectroscopic technique, or a Raman nanoscopic technique, or an infrared nanoscopic technique, or a charge dependent detection method, or a combination thereof, wherein the charge dependent detection method is chosen from the group of SEM, EDX and combinations thereof.

2. The method according to claim 1, wherein said conductive support has a top surface and a bottom surface and at least part of the top and bottom surfaces of said conductive support are substantially flat and parallel to one another or the top surface of the conductive support comprises at least a plurality of recesses having a width W and a depth D.

3. The method according to claim 1, wherein the at least one portion of said first layer possesses an area comprised between 2000 µm² and 500 µm².

4. The method according to claim 1, wherein the at least one portion of said first layer possesses an area comprised between 1500 µm² and 800 µm².

5. The method according to claim 1, wherein the conductive support is placed substantially parallel to a first horizontal plane when the heterogeneous matrix material is applied in step a) onto the at least portion of the surface of the conductive support.

6. The method according to claim 1, wherein a drying step is performed prior to the irradiation step b) thereby forming a dried layer.

7. The method according to claim 6, wherein prior or during the drying step, the conductive support is positioned from being substantially parallel to a first horizontal plane to an angle ranging from +60° to −60°, relative to a second vertical plane, even more preferably substantially parallel to a second vertical plane.

8. The method according to claim 6, wherein prior or during the drying step, the conductive support is positioned from being substantially parallel to a first horizontal plane to an angle ranging from +45° to −45°, relative to a second vertical plane, even more preferably substantially parallel to a second vertical plane.

9. The method according to claim 6, wherein prior or during the drying step, the conductive support is positioned from being substantially parallel to a first horizontal plane to an angle ranging from +30° to −30°, relative to a second vertical plane, even more preferably substantially parallel to a second vertical plane.

10. The method according to claim 6, wherein prior or during the drying step, the conductive support is positioned from being substantially parallel to a first horizontal plane to an angle ranging from +15° to −15° relative to a second vertical plane, even more preferably substantially parallel to a second vertical plane.

11. The method according to claim 6, wherein the drying step is carried out at a temperature between 30° C. and 50° C.

12. The method according to claim 1, wherein, the first layer has an average thickness of equal to or lower than 6 µm.

13. The method according to claim 1, wherein, the first layer has an average thickness of equal to or lower than 1 µm.

14. The method according to claim 1, wherein the at least portion of the first layer is irradiated with a radiation dose which varies from $1*10^{15}$ to below $1*10^{17}$ ions/cm².

15. The method according to claim 1, wherein the at least portion of the first layer is irradiated with a radiation dose which varies from above $1*10^{18}$ to below $5*10^{19}$ ions/cm².

16. The method according to claim 1, wherein the at least portion of the first layer is irradiated with a radiation dose which varies from above $5*10^{18}$ to below $5*10^{19}$ ions/cm².

17. The method according to claim 1, wherein the method further comprises a step (d) of quantifying the at least one nano or micro plastic particle comprised in the irradiated layer as formed in step b) by using, a mass spectroscopic technique, or a Raman nanoscopic technique, or an infrared nanoscopic technique, or a charge dependent detection method or a combination thereof.

18. The method according to claim 17, wherein the detection step (c) and the quantification step (d) of the micro plastic particles comprised in the irradiated layer as formed in step b) are carried out by using scanning electron microscopy.

19. The method according to claim 1, wherein the Raman based nanoscopic technique is chosen from the group consisting of Confocal Raman spectroscopy, Tip Enhanced Raman Spectroscopy, and a combination thereof, or the infrared based nanoscopic technique is nano Infrared Absorption spectroscopy or the mass spectroscopic technique is TOF-SIMS.

20. The method according to claim 1, wherein the micro or nano plastic particle is made of at least a polymer selected from the group consisting of vinyl polymers, polyurethanes, polyesters, polyethers, polyamides, polyureas, polycarbonates, polydiene, conjugated polymers, mixtures and/or copolymers thereof.

* * * * *